United States Patent
Yen et al.

(10) Patent No.: US 9,911,922 B2
(45) Date of Patent: Mar. 6, 2018

(54) ORGANIC COMPOUND FOR ELECTROLUMINESCENCE DEVICE

(71) Applicants: Feng-Wen Yen, Taipei (TW); Cheng-Hao Chang, Miao-Li (TW)

(72) Inventors: Feng-Wen Yen, Taipei (TW); Cheng-Hao Chang, Miao-Li (TW)

( * ) Notice: Subject to any disclaimer, the term of this patent is extended or adjusted under 35 U.S.C. 154(b) by 195 days.

(21) Appl. No.: 15/149,176

(22) Filed: May 8, 2016

(65) Prior Publication Data
US 2017/0324041 A1   Nov. 9, 2017

(51) Int. Cl.
*H01L 51/50*   (2006.01)
*H01L 51/00*   (2006.01)
(Continued)

(52) U.S. Cl.
CPC ........ *H01L 51/0058* (2013.01); *C07D 209/80* (2013.01); *C07D 209/86* (2013.01); *C07D 307/91* (2013.01); *C07D 333/76* (2013.01); *C09K 11/025* (2013.01); *C09K 11/06* (2013.01); *H01L 51/006* (2013.01); *H01L 51/0056* (2013.01); *H01L 51/0072* (2013.01);
(Continued)

(58) Field of Classification Search
CPC ............ H01L 51/0058; H01L 51/0059; H01L 51/0056; H01L 51/0006; H01L 51/0072; H01L 51/0073; H01L 51/0074; H01L 51/5028; C07D 209/56; C07D 209/80; C07D 209/86; C07D 307/91; C07D 307/92; C07D 333/52; C07D 333/74; C07D 333/76; C09K 11/025; C09K 11/06; C09K 2211/1007; C09K 2211/1011; C09K 2211/1014; C09K 2211/1022; C09K 2211/1029; C09K 2211/1088; C09K 2211/1092; C07C 13/62

See application file for complete search history.

(56) References Cited

U.S. PATENT DOCUMENTS 8,962,160 B2   2/2015   Yen et al.
8,993,130 B2   3/2015   Yen et al.
(Continued)

FOREIGN PATENT DOCUMENTS

WO   2008062636 A1   5/2008
WO   2012091471 A2   7/2012

*Primary Examiner* — Susan D Leong

(57) ABSTRACT

The present invention discloses an organic compound is represented by the following formula(1), the organic EL device employing the organic compound as fluorescent emitting guest shown deep blue color(CIEy=0.09~0.12)and display good performance.

formula(1)

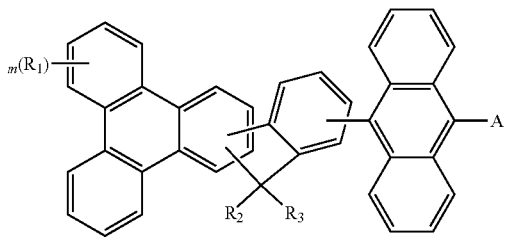

wherein A, m and $R_1$ to $R_3$ are the same definition as described in the present invention.

9 Claims, 1 Drawing Sheet

| 13 | — metal electrode |
|---|---|
| 12 | — electron injection layer |
| 11 | — electron transport layer |
| 10 | — hole blocking layer |
| 9 | — emitting layer |
| 8 | — hole transport layer |
| 7 | — hole injection layer |
| 6 | — transparent electrode |

(51) Int. Cl.
*C07D 209/80* (2006.01)
*C07D 209/86* (2006.01)
*C07D 307/91* (2006.01)
*C07D 333/76* (2006.01)
*C09K 11/02* (2006.01)
*C09K 11/06* (2006.01)

(52) U.S. Cl.
CPC ...... *H01L 51/0073* (2013.01); *H01L 51/0074* (2013.01); *C09K 2211/1007* (2013.01); *C09K 2211/1011* (2013.01); *C09K 2211/1014* (2013.01); *C09K 2211/1029* (2013.01); *C09K 2211/1088* (2013.01); *C09K 2211/1092* (2013.01); *H01L 51/5028* (2013.01)

(56) References Cited

U.S. PATENT DOCUMENTS

| | | |
|---|---|---|
| 9,040,174 B2 | 5/2015 | Yen et al. |
| 9,048,437 B2 | 6/2015 | Yen et al. |
| 9,166,177 B2 | 10/2015 | Yen et al. |
| 9,812,649 B2 * | 11/2017 | Yen ................. H01L 51/006 |
| 2013/0048975 A1 | 2/2013 | Hong et al. |
| 2014/0175383 A1 | 6/2014 | Yen et al. |
| 2016/0190472 A1 * | 6/2016 | Yen ................. H01L 51/0072 257/40 |

* cited by examiner

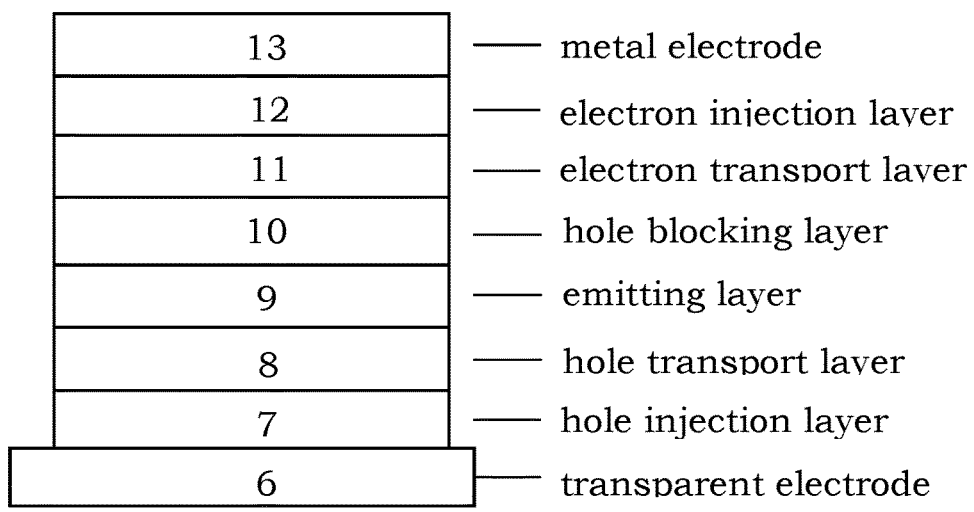

ORGANIC COMPOUND FOR ELECTROLUMINESCENCE DEVICE

FIELD OF INVENTION

The present invention generally relates to an organic compound and organic electroluminescence(herein referred to as organic EL) device using the organic material. More specifically, the present invention relates to the organic compound having general formula(1), an organic EL device employing the organic compound as fluorescent emitting guest of emitting layer.

BACKGROUND OF THE INVENTION

Organic electroluminescence(organic EL) is a light-emitting diode (LED) in which the emissive layer is a film made by organic compounds which emits light in response to an electric current. The emissive layer of organic compound is sandwiched between two electrodes. Organic EL is applied in flat panel displays due to their high illumination, low weight, ultra-thin profile, self-illumination without back light, low power consumption, wide viewing angle, high contrast, simple fabrication methods and rapid response time.

The first observation of electroluminescence in organic materials were in the early 1950s by Andre Bernanose and co-workers at the Nancy-University in France. Martin Pope and his co-workers at New York University first observed direct current(DC) electroluminescence on a single pure crystal of anthracene and on anthracene crystals doped with tetracene under vacuum in 1963.

The first diode device was reported by Ching W. Tang and Steven Van Slyke at Eastman Kodak in 1987. The device used a two-layer structure with separate hole transporting and electron transporting layers resulted in reduction in operating voltage and improvement of the efficiency, that led to the current era of organic EL research and device production.

Typically organic EL device is composed of layers of organic materials situated between two electrodes, which include a hole transporting layer(HTL), an emitting layer (EML), an electron transporting layer(ETL). The basic mechanism of organic EL involves the injection of the carrier, transport, recombination of carriers and exciton formed to emit light. When an external voltage is applied to an organic EL device, electrons and holes are injected from a cathode and an anode, respectively, electrons will be injected from a cathode into a LUMO(lowest unoccupied molecular orbital) and holes will be injected from an anode into a HOMO(highest occupied molecular orbital). When the electrons recombine with holes in the emitting layer, excitons are formed and then emit light. When luminescent molecules absorb energy to achieve an excited state, an exciton may either be in a singlet state or a triplet state depending on how the spins of the electron and hole have been combined. 75% of the excitons form by recombination of electrons and holes to achieve a triplet excited state. Decay from triplet states is spin forbidden. Thus, a fluorescence electroluminescent device has only 25% internal quantum efficiency. In contrast to fluorescence electroluminescent device, phosphorescent organic EL device make use of spin-orbit interactions to facilitate intersystem crossing between singlet and triplet states, thus obtaining emission from both singlet and triplet states and the internal quantum efficiency of electroluminescent devices from 25% to 100%.

For full-colored flat panel displays in AMOLED the material used for the fluorescent emitting layer are still unsatisfactory in half-life time, efficiency and driving voltage. In the present invention, for the purpose to prolong the half-life time and lower driving voltage for fluorescent guest in emitting layer for organic EL device, we employ an indenotriphenylene-anthracenyl skeleton link to carbazole group, dibenzothiophene group, dibenzofuran group, diarylamine group and other donor group to finish the organic compound represented as general formula(1). The organic compound show good thermal stability and charge carrier mobility for organic EL device. Indenotriphenylene skeleton based derivative disclosed in JP2013232520, KR20120072784, WO2008062636, WO2012091471, U.S. Pat. No. 8,962,160B2, U.S. Pat. No. 8,993,130B2, U.S. Pat. No. 9,040,174B2, U.S. Pat. No. 9,048,437B2 and 20140175383A1 are used for organic EL device are described. There are no prior arts demonstrate an indenotriphenylene-anthracenyl skeleton link to carbazole group, dibenzothiophene group, dibenzofuran group, diarylamine group and other donor group used as fluorescent emitting guest for organic EL device.

According to the reasons described above, the present invention has the objective of resolving such problems of the prior-art and offering a light emitting device which is excellent in its thermal stability, high luminance efficiency, high luminance and long half-life time. The present invention disclose an organic material having general formula(1), used as a fluorescent emitting guest material have good charge carrier mobility and excellent operational durability can lower driving voltage and power consumption, increasing efficiency and half-life time of organic EL device.

SUMMARY OF THE INVENTION

In accordance with the present invention, the organic compound and their use for fluorescent guest of emitting layer for organic EL device are provided. The organic compound can overcome the drawbacks of the conventional materials like as shorter half-life time, lower efficiency, higher driving voltage.

An object of the present invention is to apply the organic compound as fluorescent emitting guest for organic EL device and can lower driving voltage, lower power consumption and increase the efficiency.

The present invention has the economic advantages for industrial practice. Accordingly, the present invention discloses the organic compound which can be used for organic EL device is disclosed. The mentioned the organic compound is represented by the following formula(1)

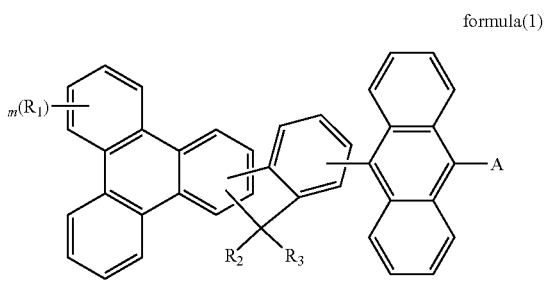

formula(1)

wherein A represents the formula(2) to formula(5)

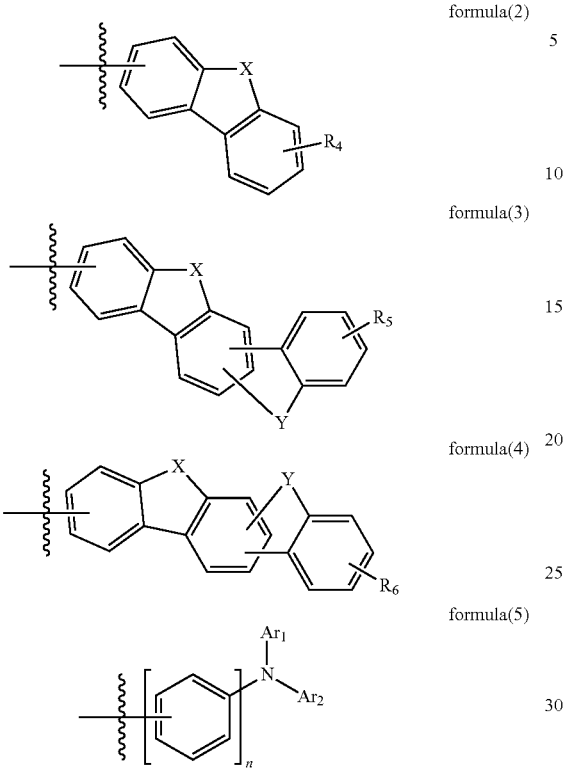

formula(2)

formula(3)

formula(4)

formula(5)

m represents an integer of 0 to 10, n represents an integer of 0 or 1, X is divalent bridge selected from the atom or group consisting from O, S and $NR_7$, Y is divalent bridge selected from the atom or group consisting from O, S, $C(R_8)(R_9)$, $Si(R_{10})(R_{11})$ and $NR_{12}$, $Ar_1$ and $R_2$ represent a substituted or unsubstituted aryl group having 6 to 30 carbon atoms, $R_1$ to $R_{12}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

BRIEF DESCRIPTION OF THE DRAWING

FIG. 1 show one example of organic EL device in the present invention, and 6 is transparent electrode, 13 is metal electrode, 7 is hole injection layer which is deposited onto 6, 8 is hole transport layer which is deposited onto 7, 9 is fluorescent emitting layer which is deposited onto 8, 10 is hole blocking layer which is deposited onto 9, 11 is electron transport layer which is deposited onto 10, and 12 is electron injection layer which is deposited on to 11.

DESCRIPTION OF THE PREFERRED EMBODIMENTS

What probed into the invention is the organic compound and organic EL device using the organic compound. Detailed descriptions of the production, structure and elements will be provided in the following to make the invention thoroughly understood. Obviously, the application of the invention is not confined to specific details familiar to those who are skilled in the art. On the other hand, the common elements and procedures that are known to everyone are not described in details to avoid unnecessary limits of the invention. Some preferred embodiments of the present invention will now be described in greater detail in the follows. However, it should be recognized that the present invention can be practiced in a wide range of other embodiments besides those explicitly described, that is, this invention can also be applied extensively to other embodiments, and the scope of the present invention is expressly not limited except as specified in the accompanying claims In a first embodiment of the present invention, the organic compound which can be used as fluorescent emitting guest for organic EL device are disclosed. The mentioned organic compound represented by the following formula(1):

formula(1)

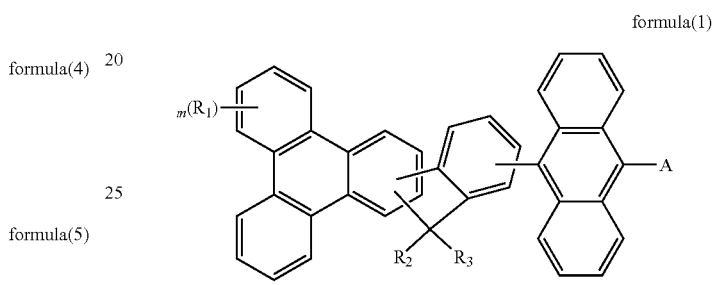

wherein A represents the formula(2) to formula(5)

formula(2)

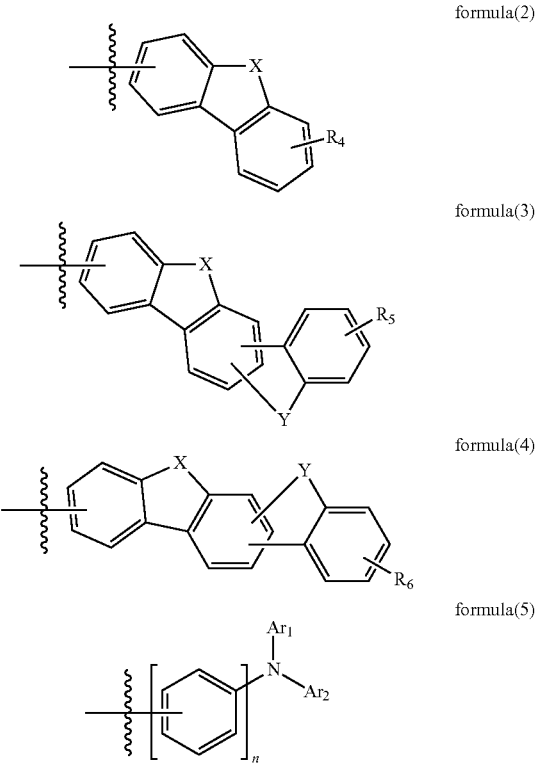

formula(3)

formula(4)

formula(5)

m represents an integer of 0 to 10, n represents an integer of 0 or 1, X is divalent bridge selected from the atom or group consisting from O, S and $NR_7$, Y is divalent bridge selected from the atom or group consisting from O, S, $C(R_8)(R_9)$, Si(R$_{10}$)(R$_{11}$) and NR$_{12}$, Ar$_1$ and Ar$_2$ represent a substituted or unsubstituted aryl group having 6 to 30 carbon atoms, R$_1$ to R$_{12}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

In this embodiment, some organic compounds are shown below:

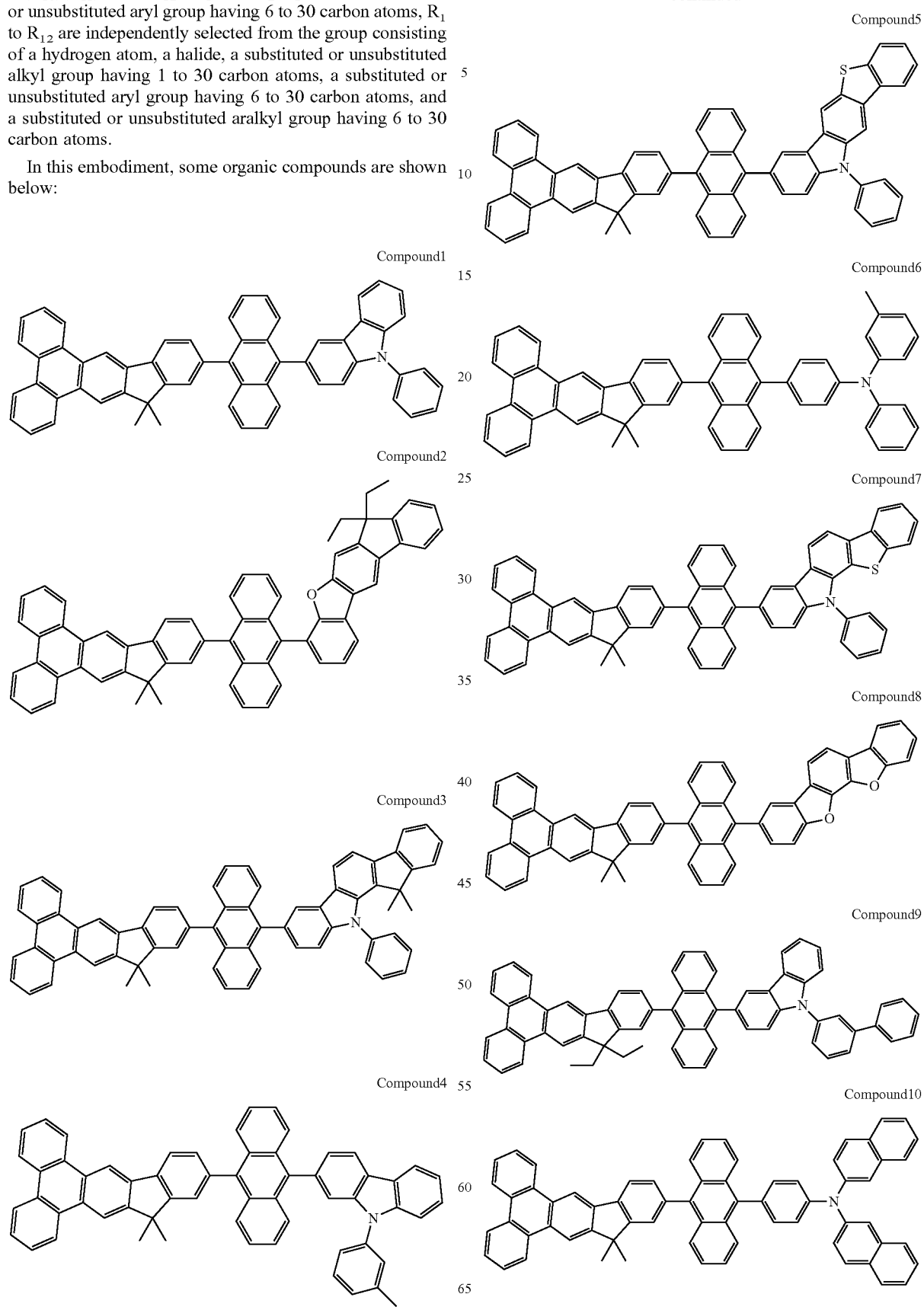

Compound11
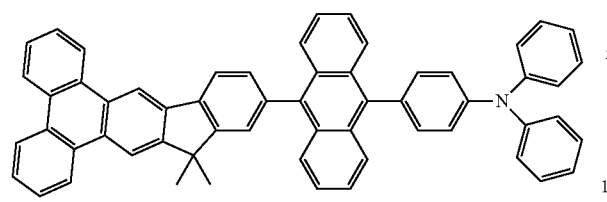
Compound12
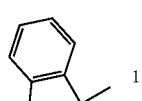
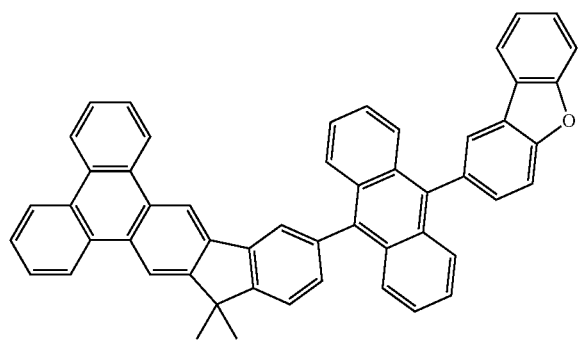
Compound16
Compound13
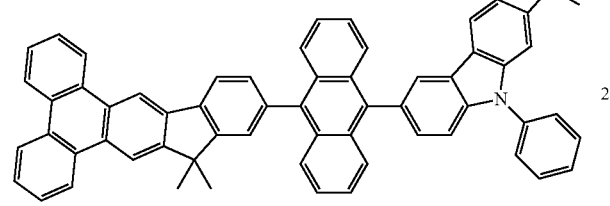
Compound17
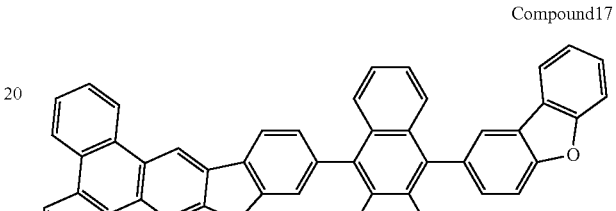
Compound14
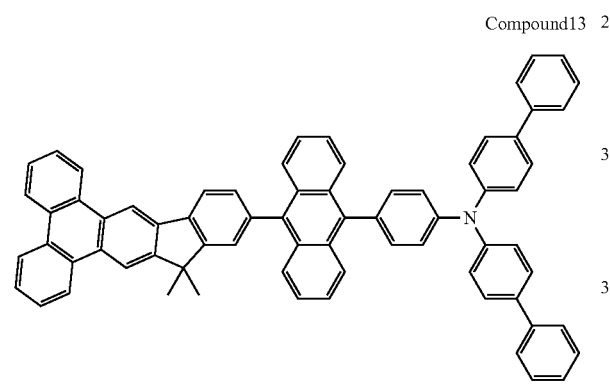
Compound18
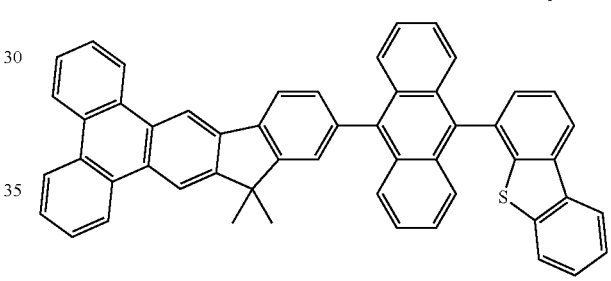
Compound19
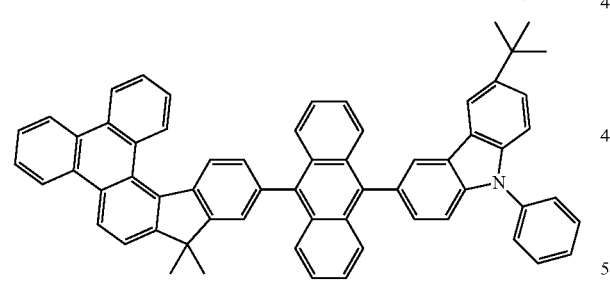
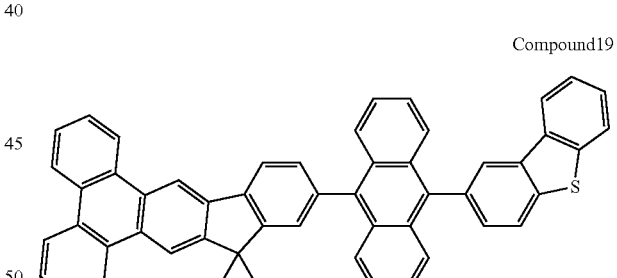
Compound15
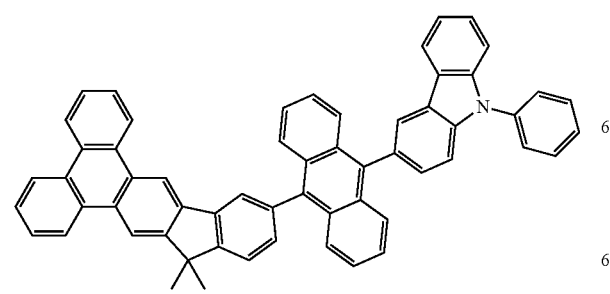
Compound20
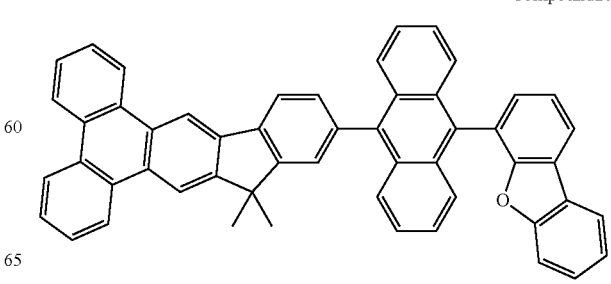

Compound21

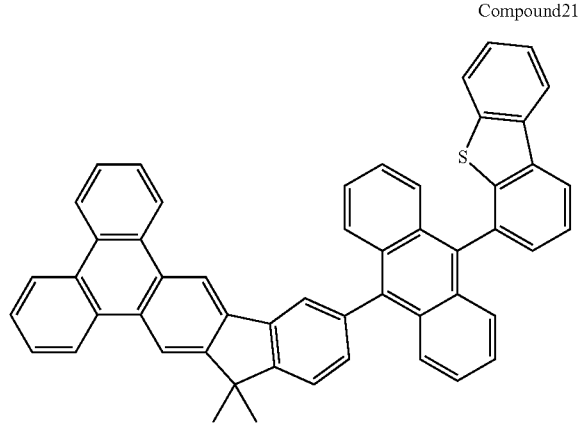

Compound22

Compound23

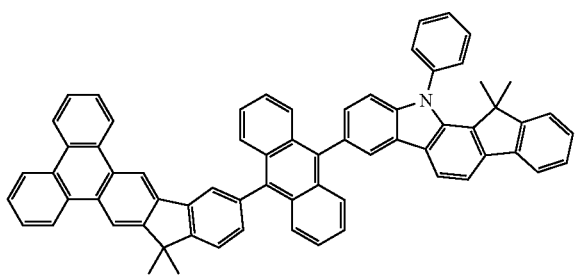

Compound24

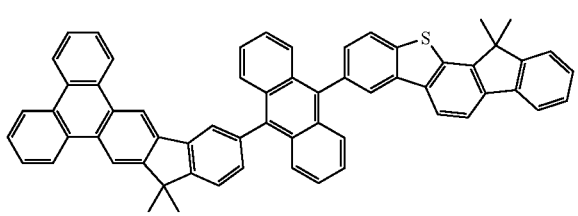

Compound25

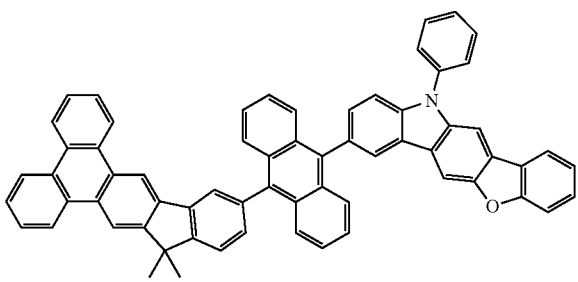

Compound26

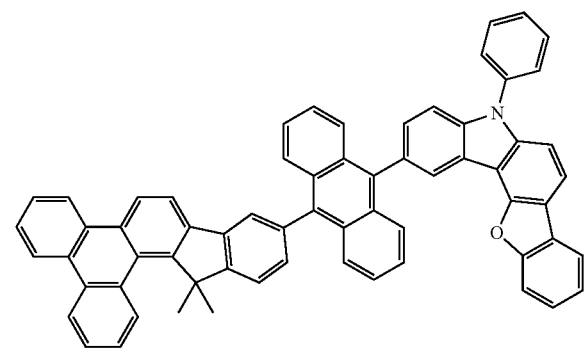

Compound27

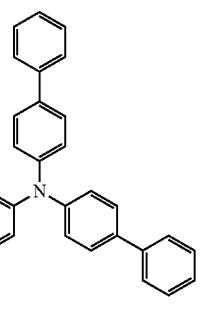

Compound28

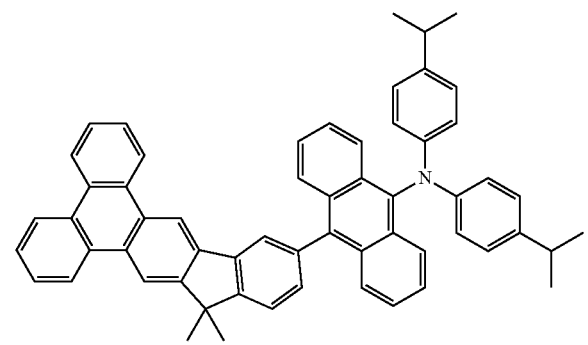

Detailed preparation for the organic compound in the present invention could be clarified by exemplary embodiments, but the present invention is not limited to exemplary embodiments. EXAMPLE 1~7 show the preparation for examples of the organic compound in the present invention. EXAMPLE 8 shows the fabrication of organic EL device and I-V-B, half-life time of organic EL device testing report.

EXAMPLE 1

Synthesis of Compound 1

Synthesis of 2-(biphenyl-2-yl)-7-bromo-9,9-dimethyl-9H-fluor-ene

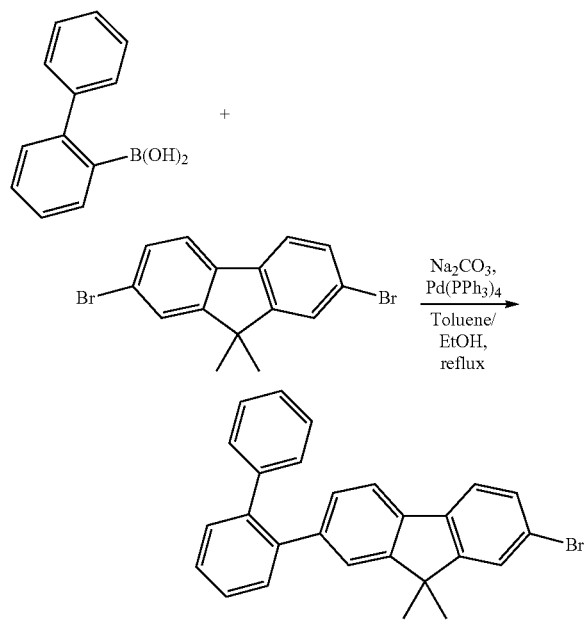

A mixture of 35.2 g(100 mmol) of 2,7-dibromo-9,9-dimethyl-9H-fluorene, 21.8 g(110 mmol) of biphenyl-2-ylboronic acid, 2.31 g(2 mmol) of Pd(PPh$_3$)$_4$, 75 ml of 2M Na$_2$CO$_3$, 150 ml of EtOH and 300 ml toluene was degassed and placed under nitrogen, and then heated at 100° C. for 12 h. After finishing the reaction, the mixture was allowed to cool to room temperature. The organic layer was extracted with ethyl acetate and water, dried with anhydrous magnesium sulfate, the solvent was removed and the residue was purified by column chromatography on silica to give product (26.8 g, 63.0 mmol, 63%) as a white solid.

Synthesis of 12-bromo-10,10-dimethyl-10H-indeno[2,1-b]triphenylene

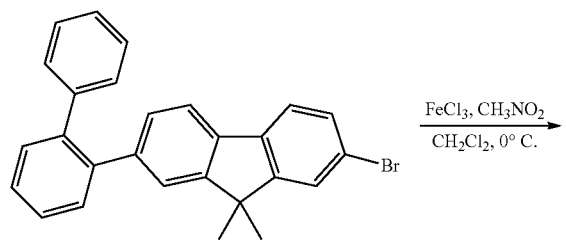

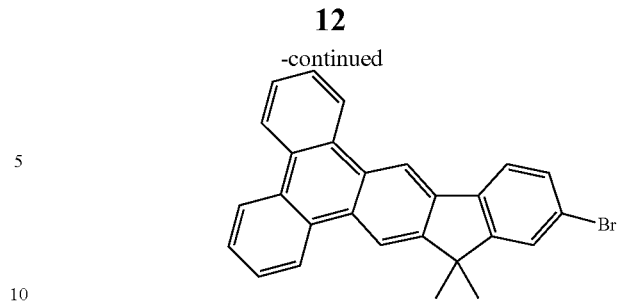

In a 3000 ml three-necked flask that had been degassed and filled with nitrogen, 26.8 g(60 mmol) of 2-(biphenyl-2-yl)-7-bromo-9,9-dimethyl-9H-fluorene was dissolved in anhydrous dichloromethane(1500 ml), 97.5 g(600 mmol) Iron(III)chloride was then added, and the mixture was stirred one hour. Methanol 500 ml were added to the mixture and the organic layer was separated and the solvent removed in vacuo. The residue was purified by column chromatography on silica(hexane-dichloromethane) afforded a white solid (10.7 g, 25.3 mmol, 40%). $^1$H NMR(CDCl3, 400 MHz): chemical shift(ppm) 8.95(s, 1H), 8.79-8.74(m, 2H), 8.69-8.68(m, 3H), 7.84(d, J=8.0 Hz, 1H), 7.72~7.65(m, 5H), 7.57(d, J=8.0 Hz, 1H), 1.66(s, 6H).

Synthesis of 2-(10,10-dimethyl-10H-indeno [2,1-b]triphenylen-12-yl)-4,4,5,5-tetramethyl-1,3,2-dioxaborolane

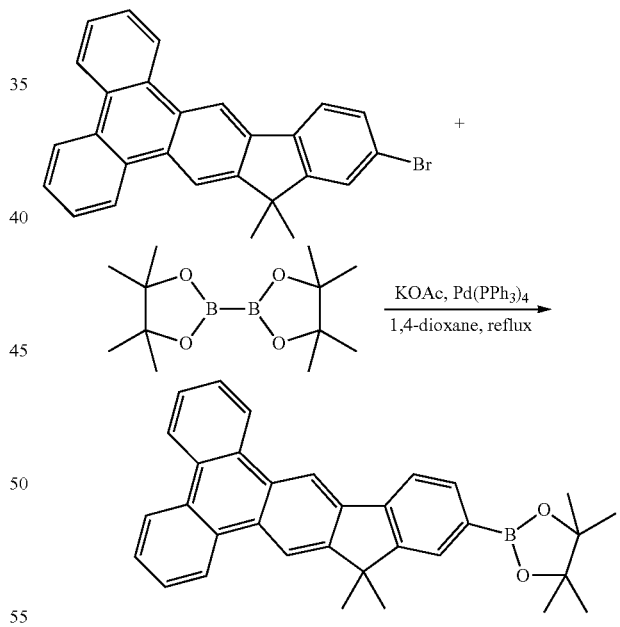

A mixture of 10.7 g(25.3 mmol) of 12-bromo-10,10-dimethyl-10H-indeno-[1,2-b]triphenylene, 7.7 g(30.3 mmol) of bis(pinacolato)diboron, 0.3 g(0.26 mmol) of Pd(PPh$_3$)$_4$, 7.4 g(75.4 mmol) of potassium acetate, and 300 ml 1,4-dioxane was degassed and placed under nitrogen, and then heated at 90° C. for 16 h. After finishing the reaction, the mixture was allowed to cool to room temperature. The organic phase separated and washed with ethyl acetate and water. After drying over magnesium sulfate, the solvent was removed in vacuo. The residue was purified by column chromatography on silica(hexane-dichloromethane) to give product(6.4 g, 13.7mmol, 54%) as a light-yellow solid; ¹H NMR(CDCl3, 400 MHz): chemical shift(ppm) 9.03(s, 1H), 8.81(d, J=7.84 Hz, 1H), 8.77(d, J=7.88 Hz, 1H), 8.70~8.67 (m, 3H), 8.02~7.93 (m, 3H), 7.71~7.67(m, 4H), 1.69(s, 6H), 1.42(s, 12H)

Synthesis of 12-(anthracen-9-yl)-10,10-dimethyl-10H-indeno [2,1-b]triphenylene

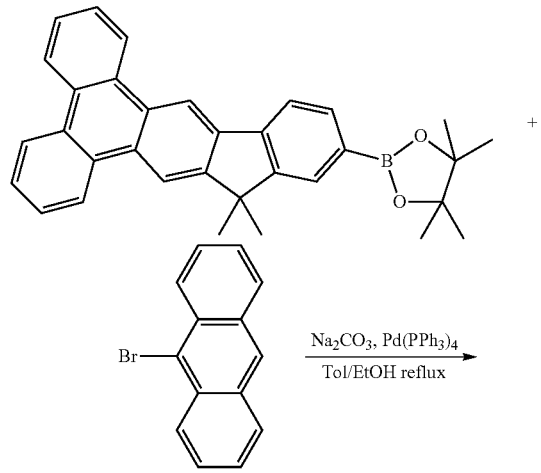

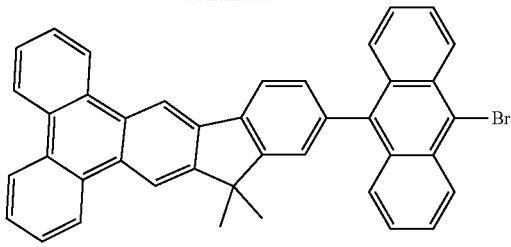

The resulting 12-(anthracen-9-yl)-10,10-dimethyl-10H-indeno [2,1-b]triphenylene(3.5 g) and DMF (35 ml) were added to a reaction vessel. N-bromosuccinimide(1.5 g) was added under ice-cooled conditions, and. the mixture was stirred for 9 hours. Water(350 ml) was added, the organic layer was extracted with dichloromethane and water, dried with anhydrous magnesium sulfate, the solvent was removed and the residue was purified by column chromatography on silica to give product(3.1 g, 5.2 mmol, 78%) as a yellow solid.

Synthesis of 3-(10-(10,10-dimethyl-10H-indeno [2,1-b] triphenylen-12-yl) anthracen-9-yl)-9-phenyl-9H-carbazole

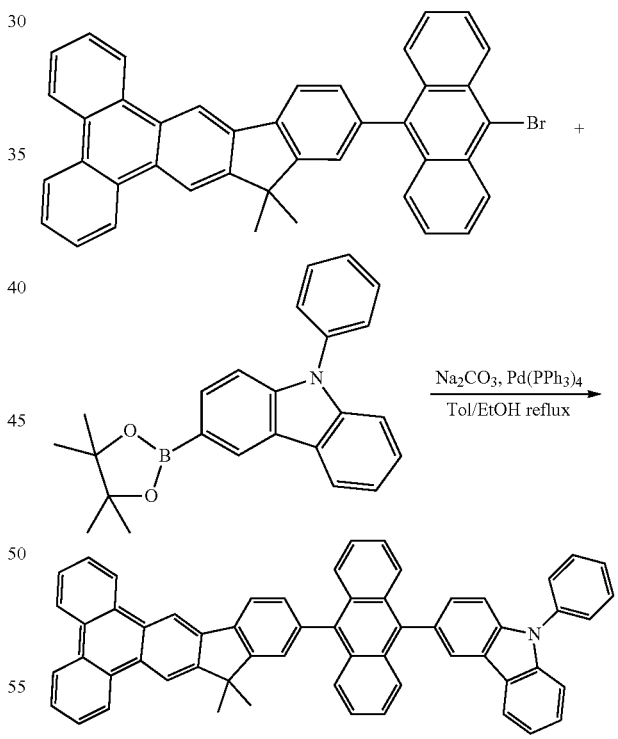

A mixture of 4.7 g(10 mmol) of 2-(10,10-dimethyl-10H-indeno[2,1-b]triphenylen-12-yl)-4,4,5,5-tetramethyl-1,3,2-dioxaborolane, 2.8 g(11 mmol) of 9-bromoanthracene, 0.22 g(0.2 mmol) of tetrakis(triphenyl phosphine)palladium, 20 ml of 2M Na₂CO₃, 20 ml of EtOH and 50 ml toluene was degassed and placed under nitrogen, and then heated at 90° C. overnight. After finishing the reaction, the mixture was allowed to cool to room temperature. Then 150 ml of MeOH was added, while stirring and the precipitated product was filtered off with suction. To give 3.5 g(yield67%) of yellow product which was recrystallized from toluene.

Synthesis of 12-(10-bromoanthracen-9-yl)-10,10-dimethyl-10H-indeno [2,1-b]triphenylene

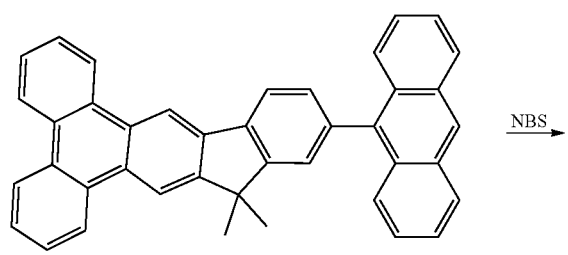

A mixture of 3.1 g(5.2 mmol) of 12-(10-bromoanthracen-9-yl)-10, 10-dimethyl-10H-indeno [2,1-b]triphenylene, 2.2 g(6 mmol) of 9-phenyl -3-(4,4,5,5-tetramethyl-1,3,2-dioxaborolan-2-yl)-9H-carbazole, 0.22 g(0.2 mmol) of tetrakis (triphenylphosphine)palladium, 20 ml of 2M Na₂CO₃, 20 ml of EtOH and 50 ml toluene was degassed and placed under nitrogen, and then heated at 110° C. overnight. After finishing the reaction, the mixture was allowed to cool to room temperature. Then 150 ml of MeOH was added, while stirring and the precipitated product was filtered off with suction. To give 2.6 g(yield 67%) of yellow product which was recrystallized from toluene. MS(m/z,FAB⁺):761.4, ¹H NMR(CDCl₃, 400 MHz): chemical shift(ppm) 9.11(s, 1H), 8.87(d, J=7.84 Hz, 1H), 8.80~8.75(m, 2H), 8.71~8.69(m, 2H), 8.28(d, J=7.84 Hz, 1H), 8.22~8.11(m, 2H), 7.88~7.82 (m, 4H), 7.76~7.63(m, 10H), 7.61~7.44(m, 5H), 7.39~7.28 (m, 5H), 1.74(s, 6H).

EXAMPLE 2

Synthesis of Compound6

Synthesis of 10-(10,10-dimethyl-10H-indeno[2,1-b]triphenylen-12-yl)-N-phenyl-N-m-tolylanthracen-9-amine

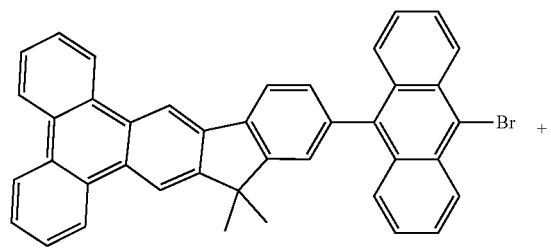

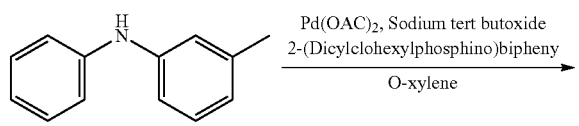

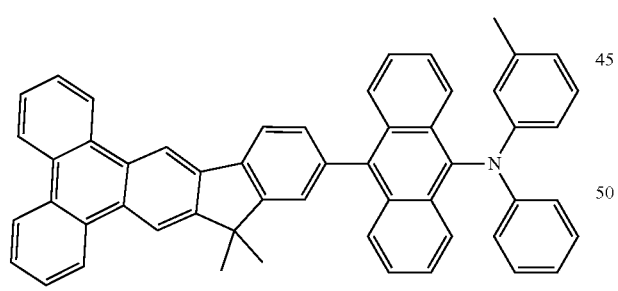

A mixture of 6.0 g(10 mmol) 12-(10-bromoanthracen-9-yl)-10,10-dimethyl-10H-indeno[2,1-b]triphenylene, 3 g(15.1 mmol) of 3-methyl-N-phenylaniline, 0.05 g(0.2 mmol) of palladium(II)acetate, 0.15 g(0.4 mmol) of 2-(dicyclohexylphosphino)biphenyl, 2 g(20 mmol)of sodium tert-butoxide and 100 ml of O-xylene was refluxed under nitrogen overnight. After finishing the reaction, the solution was filtered at 100° C., to receive the filtrate, and the filtrate was added to 1L MeOH, while stirring and the precipitated product was filtered off with suction. To give 3.1 g(yield45%) of yellow product which was recrystallized from toluene. MS(m/z, FAB⁺):701.6

EXAMPLE 3

Synthesis of Compound12

Synthesis of N-(2-chlorophenyl)-9,9-dimethyl-9H-fluoren-2-amine

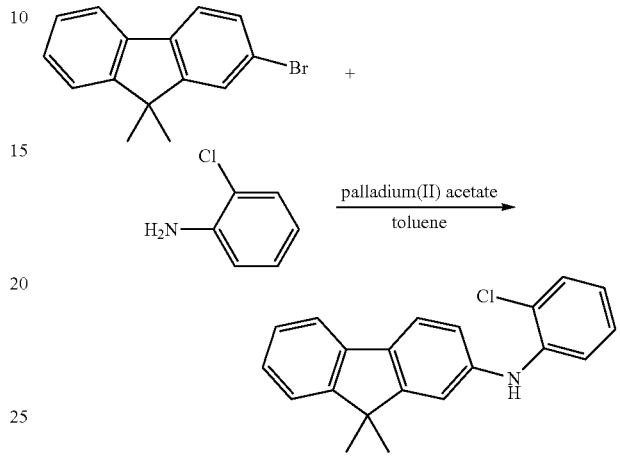

A mixture of 6.9 g(25.3 mmol) of 2-bromo-9,9-dimethyl-9H-fluorene, 3.2 g(25.3 mmol) of 2-chloroaniline, 0.11 g(0.5 mmol) of palladium(II) acetate, 0.55 g(1.0 mmol) of 1,1-bis(diphenyl-phosphino)ferrocene, 4.85 g (50.6 mmol) of sodium tert-butoxide and 100 ml toluene was degassed and placed under nitrogen, and then heated at 110° C. for overnight. After finishing the reaction, the mixture was allowed to cool to room temperature. The organic phase separated and washed with ethyl acetate and water. After drying over magnesium sulfate, the solvent was removed in vacuo. The residue was purified by column chromatography on silica gel(hexane-dichloromethane) to give product(4.9 g, 18.0 mmol, 71%) as a light-yellow solid.

Synthesis of 3,3-dimethyl-1,3-dihydroindeno[2,1-b]carbazole

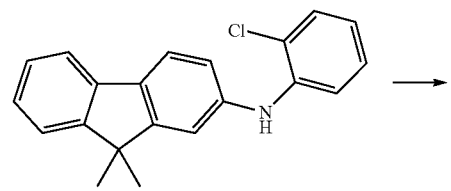

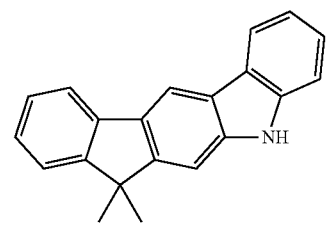

A mixture of 4.9 g(18.0 mmol) of N-(2-chlorophenyl)-9,9-dimethyl-9H-fluoren-2-amine, 0.4 g(1.6 mmol) of palladium(II) acetate, 75 ml of pivalic acid, 0.8 g of potassium carbonate (6 mmol) and 240 ml 1-methyl-2-pyrrolidone was degassed and placed under nitrogen, and then heated at 130° C. for 24 hours. After finishing the reaction, the mixture was allowed to cool to room temperature. The organic layer was extracted with dichloromethane and water, dried with anhydrous magnesium sulfate, the solvent was removed and the residue was recrystallized from hexane and dichloromethane to give product (2.1 g, 7.4 mmol, yield41%).

Synthesis of 3,3-dimethyl-1-phenyl-1,3-dihydroindeno[2,1-b] carbazole

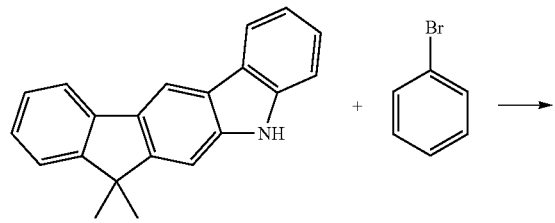

A mixture of 4.9 g(18 mmol) 3,3-dimethyl-1,3-dihydroindeno [2,1-b]carbazole, 3.4 g(21.6 mmol) of bromobenzene, 0.1 g(0.4 mmol) of palladium(II)acetate, 0.3 g(0.8 mmol) of 2-(dicyclohexylphosphino)biphenyl, 4 g(40 mmol)of sodium tert-butoxide and 50 ml of o-xylene was refluxed under nitrogen overnight. After finishing the reaction, the solution was filtered at 100° C. to receive the filtrate, and the filtrate was added to 1L MeOH, while stirring and the precipitated product was filtered off with suction. To give (4.1 g, 11.5 mmol, 64%) of yellow product which was recrystallized from toluene.

Synthesis of 10-bromo-3,3-dimethyl-1-phenyl-1,3-dihydro indeno[2,1-b]carbazole

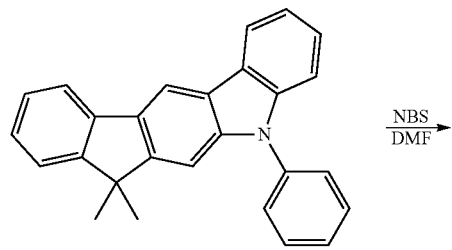

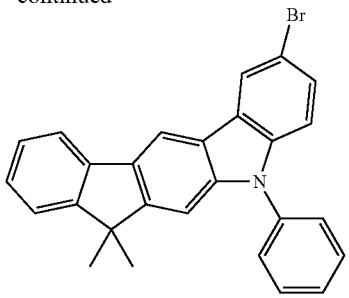

The resulting of 3,3-dimethyl-1-phenyl-1,3-dihydroindeno [2,1-b]carbazole(4.1 g) and DMF (40 ml) were added to a reaction vessel. N-bromosuccinimide(2 g) was added under ice-cooled conditions, and the mixture was stirred for 6 hours and then left for one night. 400 ml of water was added, the organic layer was extracted with dichloromethane and water, dried with anhydrous magnesium sulfate, the solvent was removed and the residue was purified by column chromatography on silica to give product(2.9 g, 6.7 mmol, 72%).

Synthesis of 3,3-dimethyl-l-phenyl-10-(4,4,5,5-tetramethyl-1,3,2-dioxaborolan-2-yl)-1,3-dihydroindeno[2,1-b]carbazole

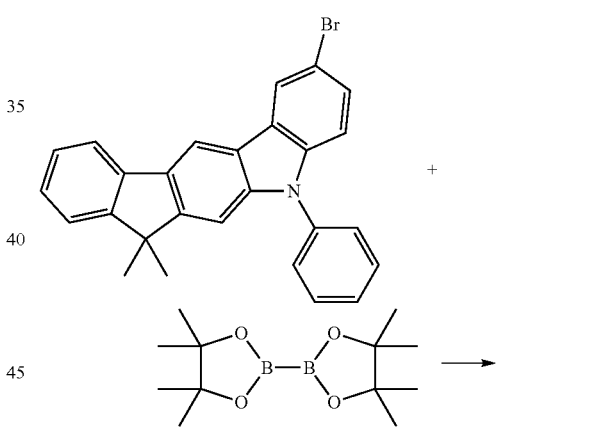

A mixture of 2.9 g(6.7 mmol) of 10-bromo-3,3-dimethyl-1-phenyl-1,3-dihydroindeno[2,1-b]carbazole, 2.2 g(8.67 mmol) of bis(pinacolato) diboron, 0.36 g(0.32 mmol) of tetrakis(triphenylphosphine)palladium, 2 g (20.28 mmol) of potassium acetate, and 300 ml of 1,4-dioxane was degassed and placed under nitrogen, and then heated at 120° C. for 16 h. After finishing the reaction, the mixture was allowed to cool to room temperature. The organic layer was extracted with ethyl acetate and water, dried with anhydrous magnesium sulfate, the solvent was removed and the product was purified by column using a mixture of hexanes and ethyl acetate as eluent to get 2.4 g of light yellow product (yield76%).

Synthesis of 10-(10-(10,10-dimethyl-10H-indeno[2,1-b] triphenylen-12-yl)anthracen-9-yl)-3,3-dimethyl-1-phenyl-1,3-dihydroindeno[2,1-b] carbazole

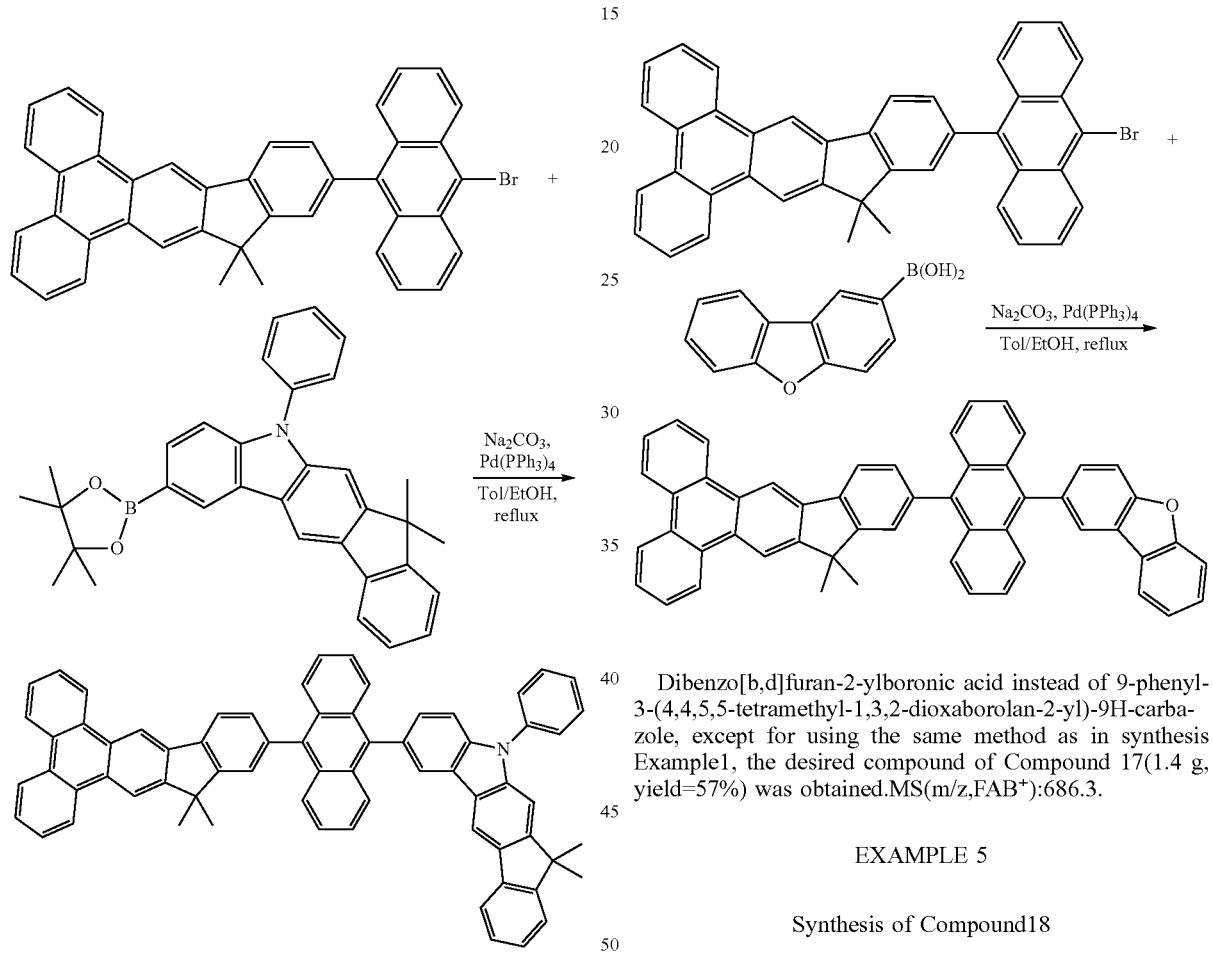

A mixture of 3. g(5 mmol) of 12-(10-bromoanthracen-9-yl)-10, 10-dimethyl-10H-indeno[2,1-b]triphenylene, 2.4 g(5 mmol) of 3,3-dimethyl-1-phenyl-10-(4,4,5,5-tetramethyl-1,3,2-dioxaborolan-2-yl)-1,3-dihydroinden o[2,1-b]carbazole, 0.22 g(0.2 mmol) of tetrakis(triphenyl phosphine)palladium, 20 ml of 2M Na$_2$CO$_3$, 20 ml of EtOH and 50 ml toluene was degassed and placed under nitrogen, and then heated at 110° C. overnight. After finishing the reaction, the mixture was allowed to cool to room temperature. Than 150 ml of MeOH was added, while stirring and the precipitated product was filtered off with suction. To give 2.6 g (yield67%) of yellow product which was recrystallized from toluene. MS(m/z, FAB$^+$):877.6, $^1$H NMR (CDCl$_3$, 400 MHz): chemical shift (ppm) 9.13(s, 1H), 8.85(d, J=7.84 Hz, 1H), 8.78~8.74(m, 2H), 8.73~8.68(m, 2H), 8.28~8.24(m, 3H), 8.22~8.11(m, 2H), 7.88~7.82(m, 4H), 7.76~7.63(m, 10H), 7.62~7.43(m, 5H), 7.38~7.28(m, 5H), 1.74(s, 6H), 1.57(s, 6H).

EXAMPLE 4

Synthesis of Compound17

Synthesis of 2-(10-(10,10-dimethyl-10H-indeno[2,1-b] triphenylen-12-yl)anthracen-9-yl)dibenzo[b,d]furan

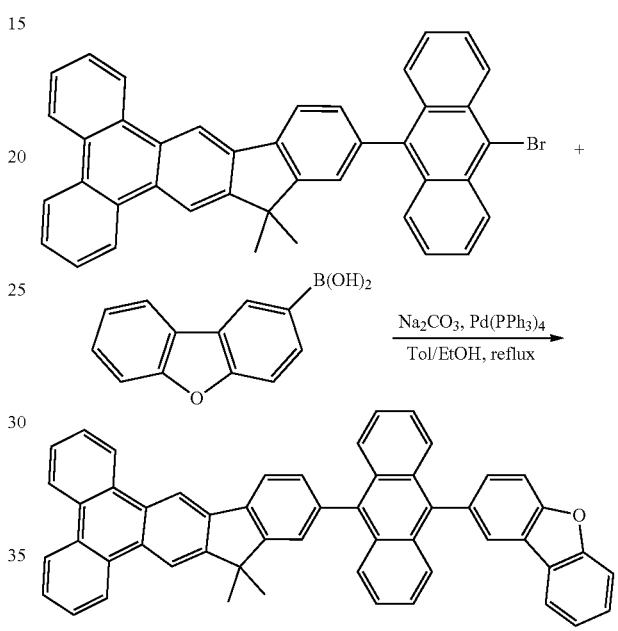

Dibenzo[b,d]furan-2-ylboronic acid instead of 9-phenyl-3-(4,4,5,5-tetramethyl-1,3,2-dioxaborolan-2-yl)-9H-carbazole, except for using the same method as in synthesis Example1, the desired compound of Compound 17(1.4 g, yield=57%) was obtained.MS(m/z,FAB$^+$):686.3.

EXAMPLE 5

Synthesis of Compound18

Synthesis of 4-(10-(10,10-dimethyl-10H-indeno[2,1-b] triphenylen-12-yl)anthracen-9-yl)dibenzo[b,d]thiophene

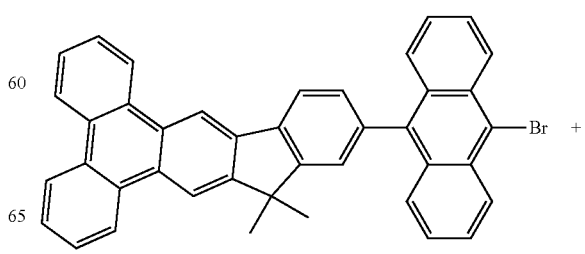

-continued

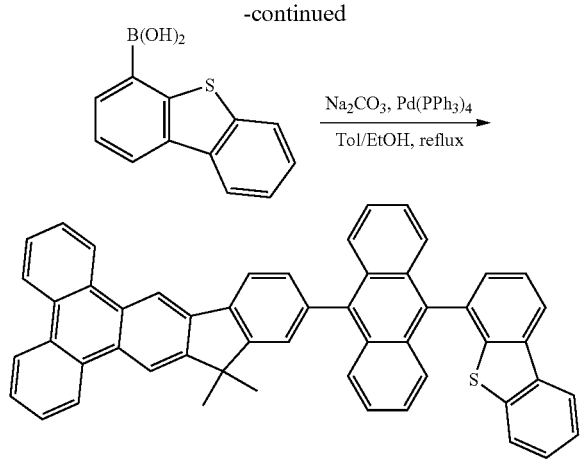

Dibenzo[b,d]thiophen-4-ylboronic acid instead of 9-phenyl-3-(4,4,5,5-tetramethyl-1,3,2-dioxaborolan-2-yl)-9H-carbazole, except for using the same method as in synthesis Example1, the desired compound of Compound18 yield=68%) was obtained. MS(m/z,FAB+):720.8.

EXAMPLE 6

Synthesis of Compound19

Synthesis of 4-(10-(10,10-dimethyl-10H-indeno[2,1-b] triphenylen-12-yl)anthracen-9-yl)dibenzo[b,d]thiophene

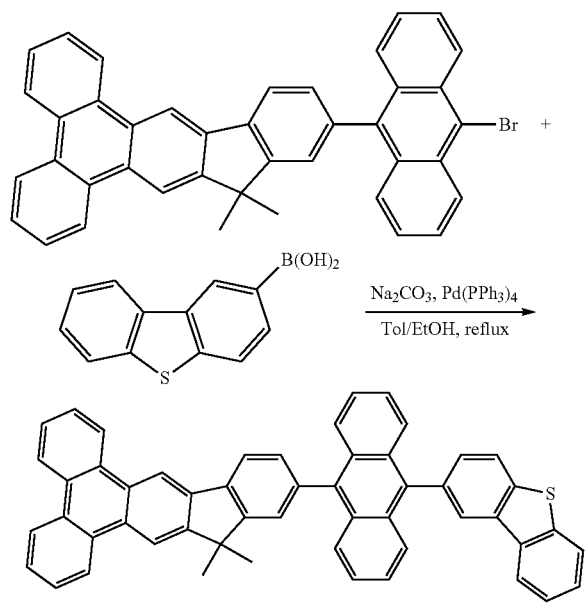

Dibenzo[b,d]thiophen-4-ylboronic acid instead of 9-phenyl-3-(4,4,5, 5-tetramethyl-1,3,2-dioxaborolan-2-yl)-9H-carbazole, except for using the same method as in synthesis Example 1, the desired compound of Compound19 (1.8 g, yield=68%) was obtained. MS(m/z,FAB+):720.8.

EXAMPLE 7

Synthesis of Compound20

Synthesis of 4-(10-(10,10-dimethyl-10H-indeno[2,1-b]triphenyl en-12-yl)anthracen-9-yl)dibenzo [b,d] furan

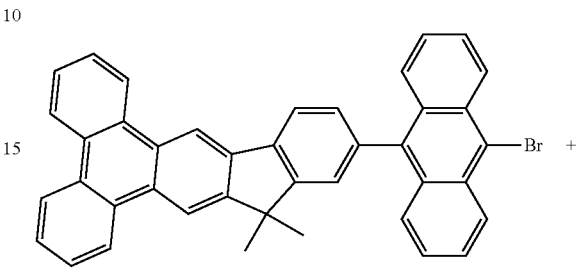

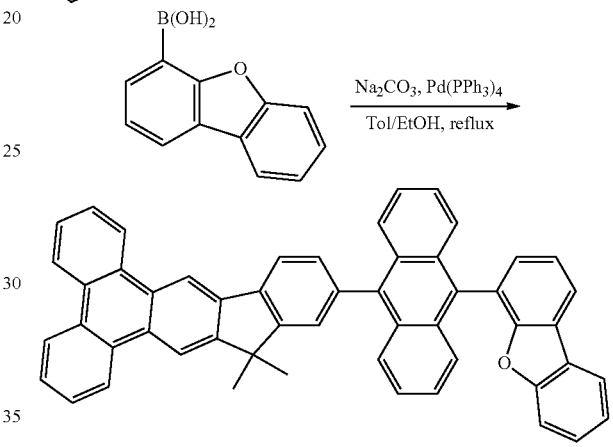

Dibenzo[b,d]furan-4-ylboronic acid instead of 9-phenyl-3-(4,4,5,5-tetramethyl-1,3,2-dioxaborolan-2-yl)-9H-carbazole, except for using the same method as in synthesis Example1, the desired compound of Compound20 (2.6 g, yield=53%) was obtained. MS(m/z,FAB+):686.4.

General Method of Producing Organic El Device

ITO-coated glasses with 9-12 ohm/square in resistance and 120~160 nm in thickness are provided(hereinafter ITO substrate) and cleaned in a number of cleaning steps in an ultrasonic bath(e.g. detergent, deionized water). Before vapor deposition of the organic layers, cleaned ITO substrates are further treated by UV and ozone. All pre-treatment processes for ITO substrate are under clean room(class 100).

These organic layers are applied onto the ITO substrate in order by vapor deposition in a high-vacuum unit($10^{-7}$ Torr), such as: resistively heated quartz boats. The thickness of the respective layer and the vapor deposition rate (0.1~0.3 nm/sec) are precisely monitored or set with the aid of a quartz-crystal monitor. It is also possible, as described above, for individual layers to consist of more than one compound, i.e. in general a host material doped with a dopant material. This is achieved by co-vaporization from two or more sources.

Dipyrazino [2,3-f:2,3-]quinoxaline-2,3,6,7,10,11-hexacarbonitrile (HAT-CN) is used as hole injection layer in this organic EL device, N,N-Bis (naphthalene-1-yl)-N,N-bis (phenyl)-benzidine(NPB) is most widely used as the hole transporting layer; 10, 10-dimethyl-12-(10-(4-(naphthalene-1-yl)phenyl) anthracen-9-yl)-10H-indeno [2,1-b]triphenylene (H3) and 10, 10-dimethyl-13-(10-(3-(naphthalen-2-yl)phenyl)anthracen-9-yl)-10H-indeno [2,1-b]triphenylene(H4) are used as emitting host in organic EL device and N1,N1,N6,N6-tetram-tolylpyrene-1,6-diamine(D1) is used as blue guest for comparison; HB3(see the following chemical structure) are used as hole blocking material(HBM) and 1-(4-(10-(naphthalen-2-yl)anthracen-9-yl)phenyl)-2-phenyl-1H-benzo[d]imidazole(ET2) is used as electron transporting material to co-deposit with 8-hydroxyquinolato-lithium(LiQ) in organic EL device. The prior art of OLED materials for producing standard organic EL device control and comparable material in this invention shown its chemical structure as follows:

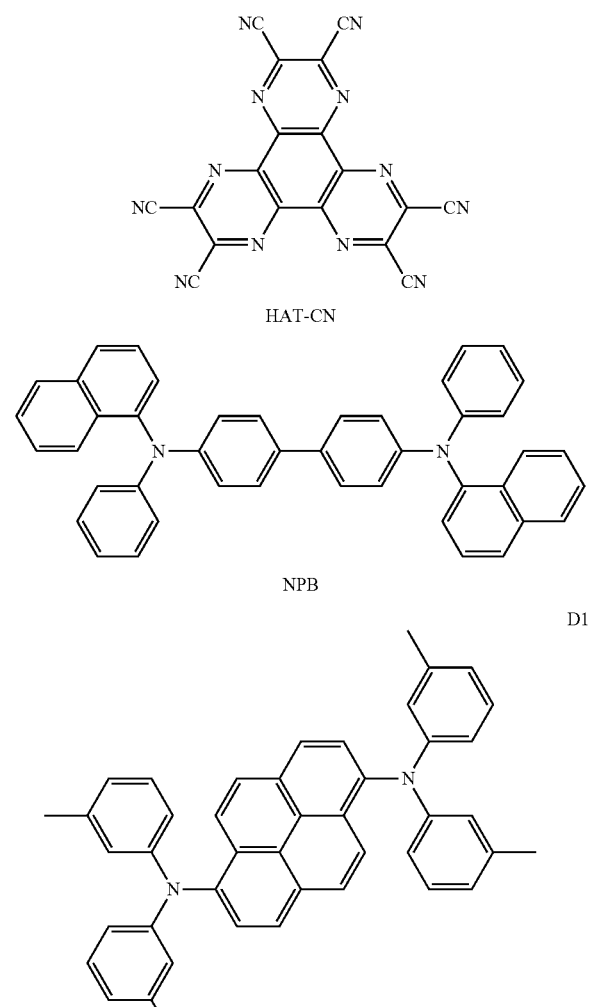

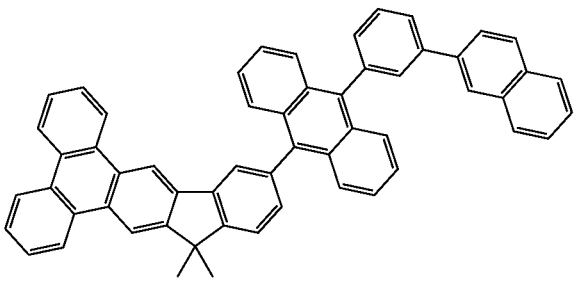

H4

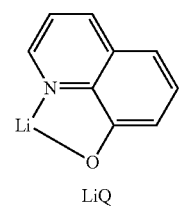

LiQ

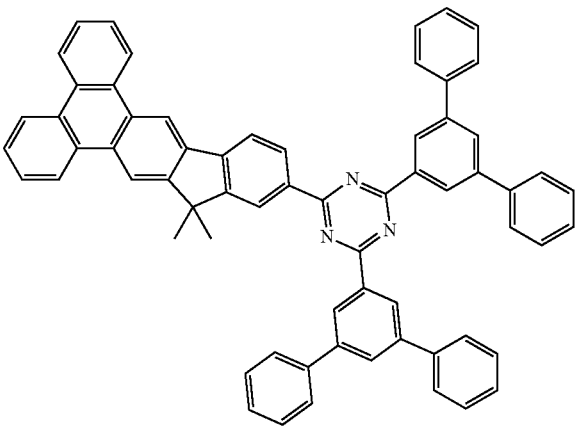

HB3

ET1

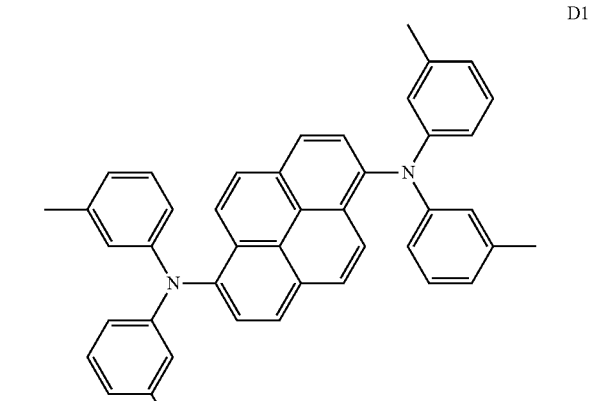

H3

Compound1

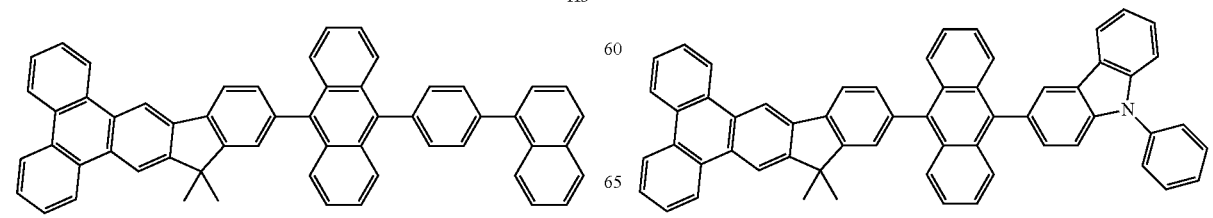

-continued

Compound6

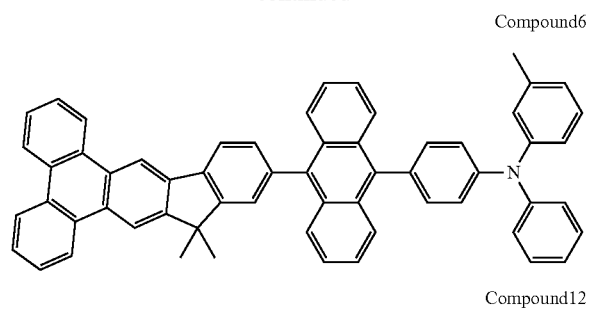

Compound12

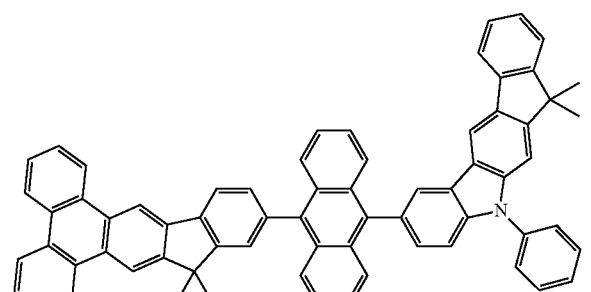

Compound17

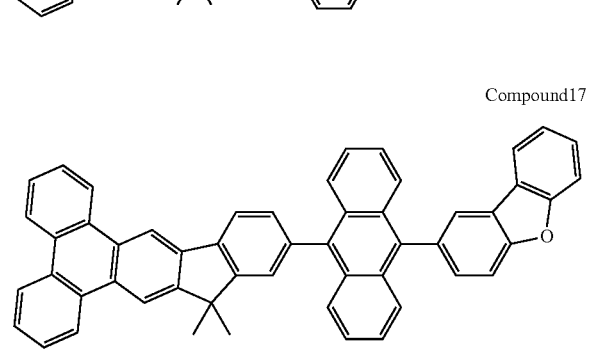

Compound18

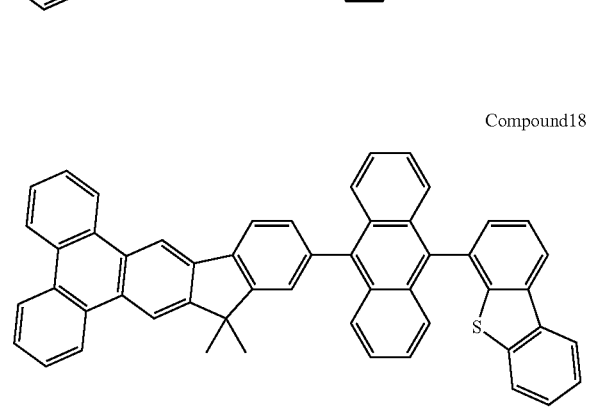

Compound19

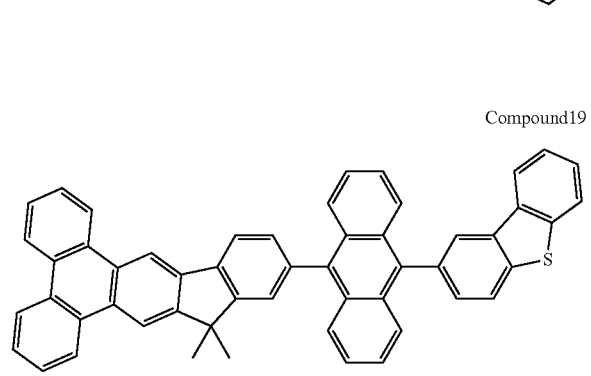

-continued

Compound20

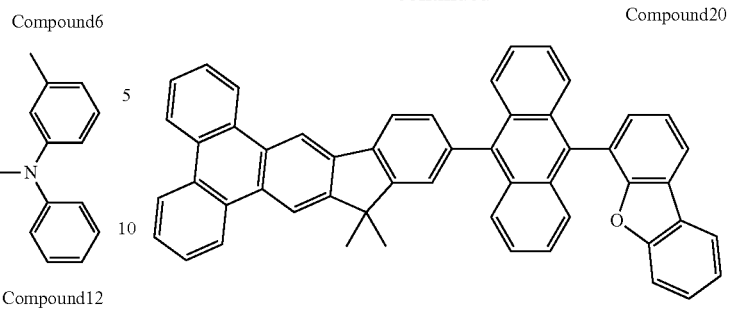

A typical organic EL device consists of low work function metals, such as Al, Mg, Ca, Li and K, as the cathode by thermal evaporation, and the low work function metals can help electrons injecting the electron transporting layer from cathode. In addition, for reducing the electron injection barrier and improving the organic EL device performance, a thin-film electron injecting layer is introduced between the cathode and the electron transporting layer. Conventional materials of electron injecting layer are metal halide or metal oxide with low work function, such as: LiF, LiQ, MgO, or $Li_2O$. On the other hand, after the organic EL device fabrication, EL spectra and CIE coordination are measured by using a PR650 spectra scan spectrometer. Furthermore, the current/voltage, luminescence/voltage and yield/voltage characteristics are taken with a Keithley 2400 programmable voltage-current source. The above-mentioned apparatuses are operated at room temperature(about 25° C.) and under atmospheric pressure.

EXAMPLE 8

Using a procedure analogous to the above mentioned general method, fluorescent emitting organic EL device having the following device structure was produced(See FIG. 1). Device: ITO/HAT-CN(20 nm)/NPB (110 nm)/Emitting host doped 5% Emitting guest(30 nm)/HB3/ET2 doped 50%LiQ(35 nm)/LiQ(1 nm)/Al(160 nm). The I-V-B(at 1000 nits) and half-life time of fluorescent emitting organic EL device testing report as Table 1. The half-life time is defined that the initial luminance of 1000 $cd/m^2$ has dropped to half.

TABLE 1

| Emitting Host | Emitting Guest | Voltage (V) | Efficiency (cd/A) | CIE (y) | Half-life time (hour) |
|---|---|---|---|---|---|
| H3 | D1 | 5.0 | 5.6 | 0.18 | 450 |
| H3 | C1 | 4.5 | 4.8 | 0.11 | 380 |
| H3 | C6 | 4.8 | 4.6 | 0.10 | 350 |
| H3 | C12 | 4.8 | 4.5 | 0.09 | 480 |
| H3 | C17 | 5.0 | 4.4 | 0.12 | 220 |
| H3 | C18 | 4.5 | 4.0 | 0.11 | 180 |
| H3 | C19 | 4.5 | 3.8 | 0.11 | 250 |
| H3 | C20 | 4.5 | 4.2 | 0.12 | 280 |
| H4 | D1 | 5.5 | 5.2 | 0.19 | 420 |
| H4 | C1 | 4.8 | 4.2 | 0.11 | 300 |
| H4 | C6 | 4.5 | 4.6 | 0.09 | 250 |
| H4 | C12 | 5.0 | 4.0 | 0.10 | 400 |
| H4 | C17 | 4.8 | 4.5 | 0.11 | 200 |
| H4 | C18 | 4.6 | 4.2 | 0.12 | 110 |
| H4 | C19 | 4.8 | 3.6 | 0.12 | 200 |
| H4 | C20 | 4.5 | 4.0 | 0.12 | 240 |

In the above preferred embodiments for organic EL device test report(see Table 1), we show that the organic compound with a general formula(1) used as emitting guest material for organic EL in the present invention display good performance. More specifically, the organic EL device in the present invention use the organic compound with a general formula(1) as emitting guest material to collocate with emitting host material such as H3 and H4 shown lower power consumption, higher efficiency and longer half-life time.

To sum up, the present invention discloses an organic compound with a general formula(1) used as emitting guest material for organic EL device. The mentioned organic compound are represented by the following formula(1)

formula(1)

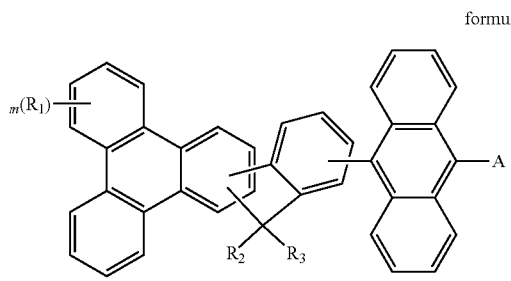

wherein A represents the formula(2) to formula(5)

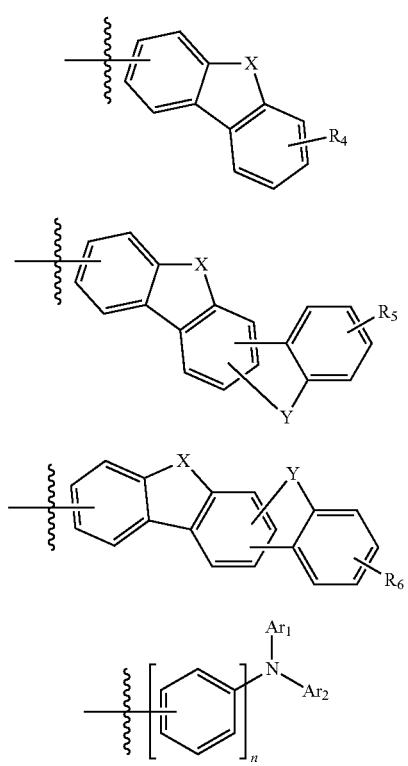

m represents an integer of 0 to 10, n represents an integer of 0 or 1, X is divalent bridge selected from the atom or group consisting from O, S and $NR_7$, Y is divalent bridge selected from the atom or group consisting from O, S, $C(R_8)(R_9)$, $Si(R_{10})(R_{11})$ and $NR_{12}$, $Ar_1$ and $Ar_2$ represent a substituted or unsubstituted aryl group having 6 to 30 carbon atoms, $R_1$ to $R_{12}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

Obvious many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

The invention claimed is:
1. A organic compound with a general formula(1) as follows:

formula(1)

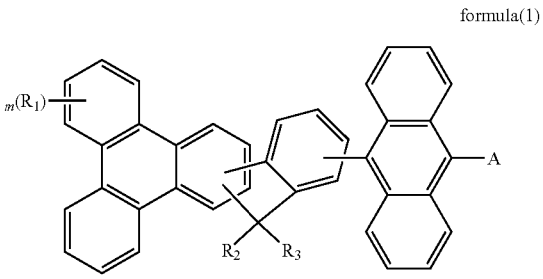

wherein A represents the one of formula(2) to formula(5)

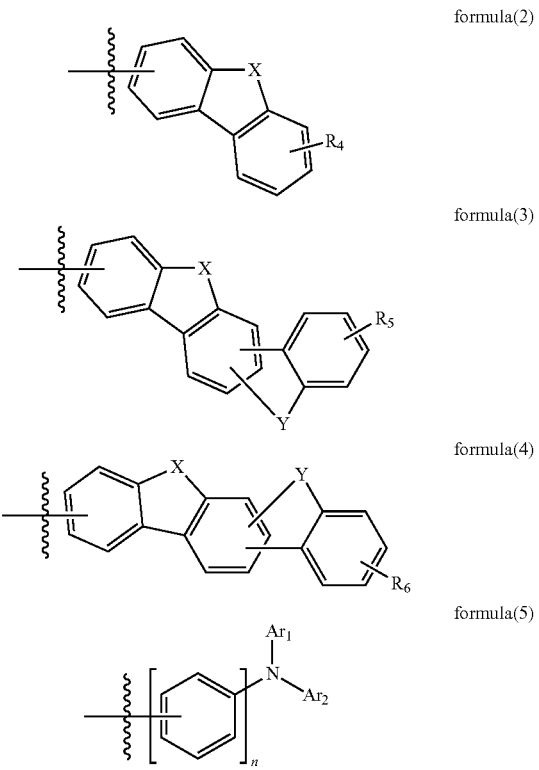

m represents an integer of 0 to 10, n represents an integer of 0 or 1, X is divalent bridge selected from the atom or group consisting from O, S and $NR_7$, Y is divalent bridge selected from the atom or group consisting from O, S, C(R$_8$)(R$_9$), Si(R$_{10}$)(R$_{11}$) and NR$_{12}$, Ar$_1$ and Ar$_2$ represent a substituted or unsubstituted aryl group having 6 to 30 carbon atoms, R$_1$ to R$_{12}$ are independently selected from the group consisting of a hydrogen atom, a halide, a substituted or unsubstituted alkyl group having 1 to 30 carbon atoms, a substituted or unsubstituted aryl group having 6 to 30 carbon atoms, and a substituted or unsubstituted aralkyl group having 6 to 30 carbon atoms.

2. The organic compound according to claim 1, wherein the organic compound is selected from the group consist of:

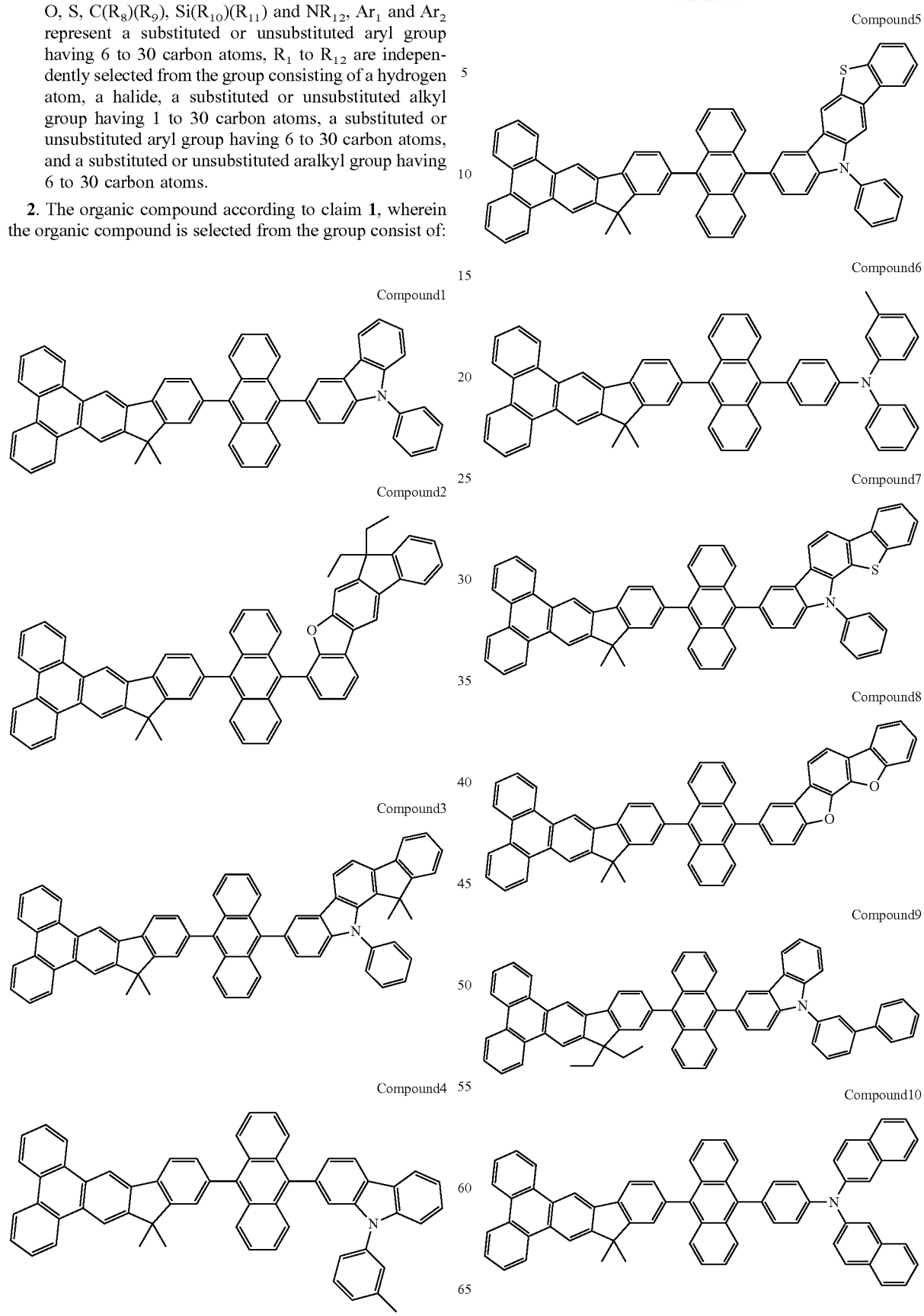

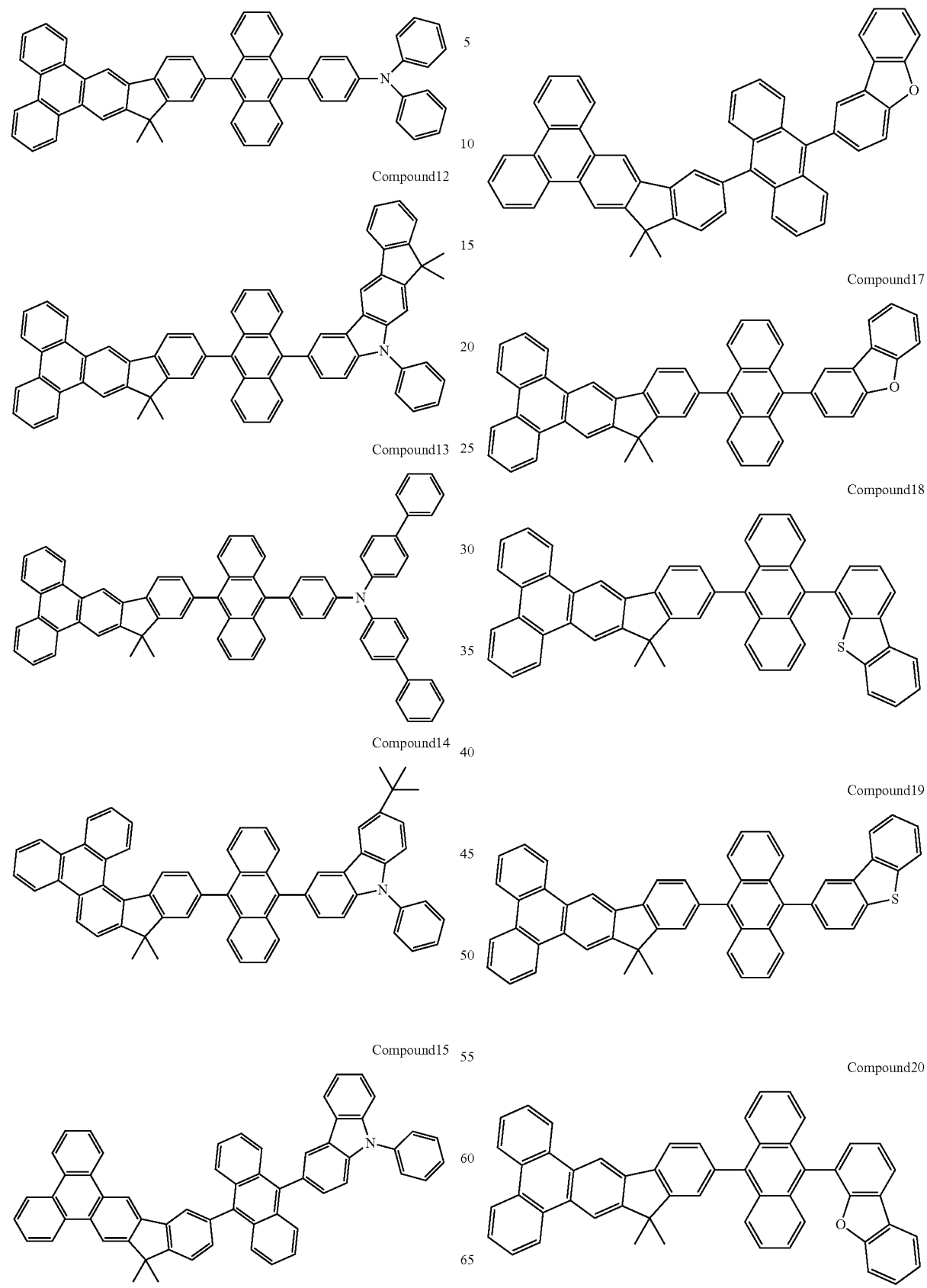

Compound21
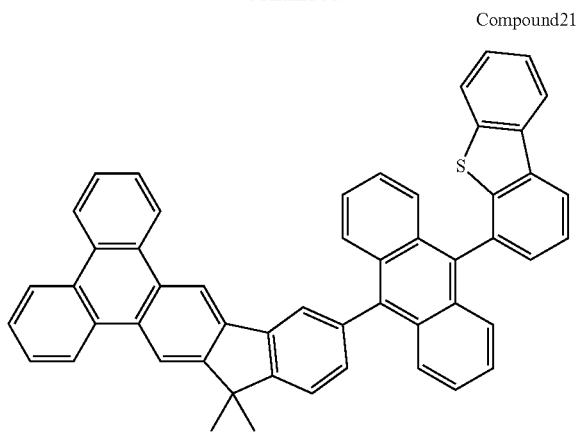

Compound22

Compound23

Compound24
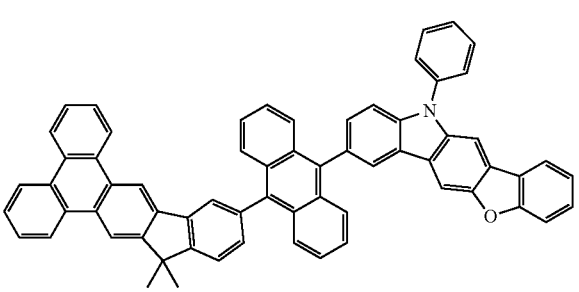

Compound25
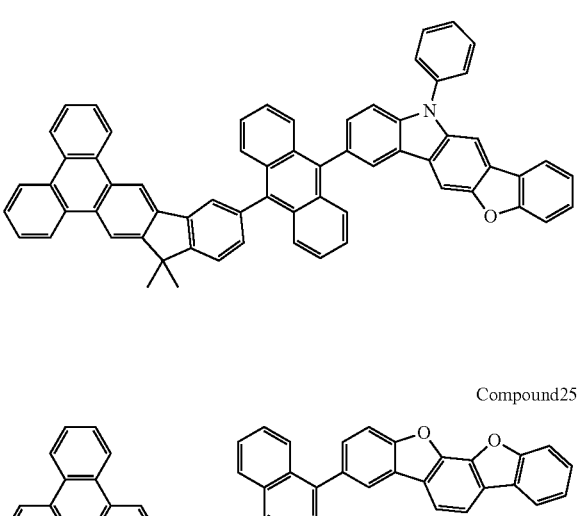

Compound26
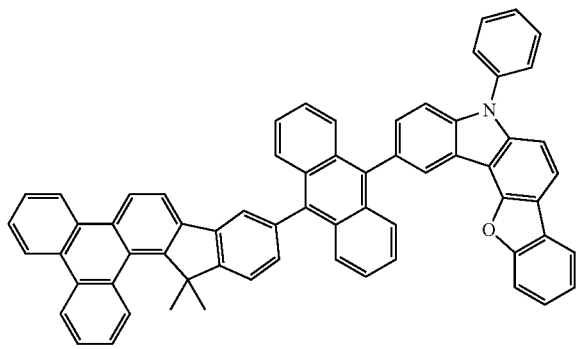

Compound27
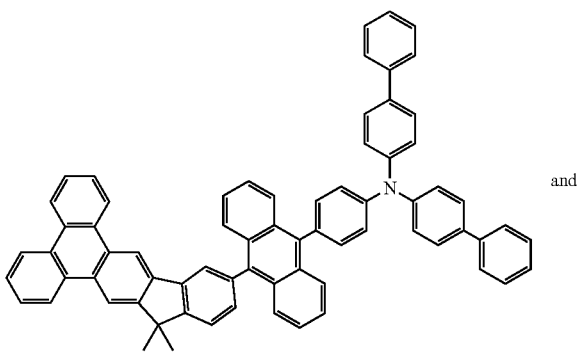

and

Compound28
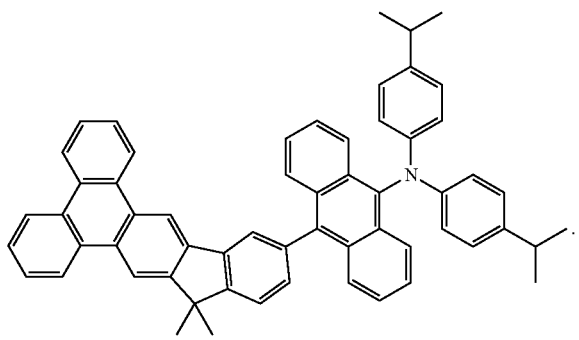

3. A organic electroluminescence device comprising a pair of electrodes consisting of a cathode and an anode, and between the pairs of electrodes comprising at least a light emitting layer, one or more layers of organic thin film layer, wherein the light emitting layer comprising the organic compound according to claim 1.

4. The organic electroluminescence device according to claim 3, wherein the light emitting layer comprising the organic compound with a general formula(1) is a guest material.

5. The organic electroluminescence device according to claim 3, wherein the light emitting layer comprising the organic compound with a general formula(1) is a fluorescent emitter.

6. The organic electroluminescence device according to claim 3, wherein the light emitting layer emits fluorescent blue lights.

7. The organic electroluminescence device according to claim 3, wherein the device is an organic light emitting device.

8. The organic electroluminescent device according to claim 3, wherein the device is a lighting panel.

9. The organic electroluminescent device according to claim 3, wherein the device is a backlight panel.

* * * * *